US009204599B2

(12) United States Patent
Cui et al.

(10) Patent No.: US 9,204,599 B2
(45) Date of Patent: Dec. 8, 2015

(54) DETECTION OF AAD1 EVENT DAS-40278-9

(75) Inventors: Yunxing Cory Cui, Carmel, IN (US); Thomas William Greene, Zionsville, IN (US); Stephen Novak, Westfield, IN (US); Ning Zhou, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 654 days.

(21) Appl. No.: 13/390,979

(22) PCT Filed: Aug. 18, 2010

(86) PCT No.: PCT/US2010/045871
§ 371 (c)(1),
(2), (4) Date: Jun. 1, 2012

(87) PCT Pub. No.: WO2011/022471
PCT Pub. Date: Feb. 24, 2011

(65) Prior Publication Data
US 2012/0244533 A1    Sep. 27, 2012

Related U.S. Application Data

(60) Provisional application No. 61/327,366, filed on Apr. 23, 2010, provisional application No. 61/235,248, filed on Aug. 19, 2009.

(51) Int. Cl.
*A01H 1/04* (2006.01)
*C12N 15/82* (2006.01)
*C12Q 1/68* (2006.01)

(52) U.S. Cl.
CPC .............. *A01H 1/04* (2013.01); *C12N 15/8274* (2013.01); *C12Q 1/6895* (2013.01); *C12Q 2561/101* (2013.01); *C12Q 2600/13* (2013.01)

(58) Field of Classification Search
None
See application file for complete search history.

(56) References Cited

U.S. PATENT DOCUMENTS

| 2002/0073448 A1 | 6/2002 | Michalowski et al. |
| 2007/0089201 A1 | 4/2007 | Briggs et al. |
| 2009/0093366 A1 | 4/2009 | Wright et al. |

FOREIGN PATENT DOCUMENTS

| WO | WO2005059103 | 6/2005 |
| WO | WO2005107437 | 11/2005 |
| WO | WO 2005107437 A2 * | 11/2005 |

OTHER PUBLICATIONS

German et al.: 'A rapid method for the analysis of zygosity in transgenic plants. Plant Science vol. 164, No. 2, Feb. 2003, pp. 183-187, XP008154095.
Yang et al.: 'Event Specific Qualitative and Quantitative Polymerase Chain Reaction Detection of Genetically Modified MON863 Maize Based on the 5'-Transgene Integration Sequence.' J Agric Food Chem vol. 53, No. 24, Nov. 30, 2005, pp. 9312-9318, XP008154145 DOI: http://dx.doi.org/10.1021/if051782o.
Brodmann et al.: 'Real-Time Quantitative Polymerase Chain Reaction Methods for Four Genetically Modified Maize Varieties and Maize DNA Content in Food.' Journal of AOAC International vol. 85, No. 3, May 2002, pp. 646-653, XP008154098.
Sylvain et al.: 'Rapid screening for HLA-B27 by a TaqMan-PCR assay using sequence-specific primers and a minor groove binder probe, a novel type of TaqMan probe.' Journal of Immunological Methods vol. 287, No. 1-2, Apr. 2004, pp. 178-186, XP008154147 DOI: http://dx.doi.org/10.1016/j.jim.2004.01.027.
Gotsch et al.: 'Nuclease-Resistant Single-Stranded DNA Controls for Nucleic Acid Amplification Assays.' J Clin Microbiol vol. 45, No. 8, Aug. 2007, pp. 2570-2574, XP008154099.
'Abi Prism 7000 Sequence Detection System and Applied Biosystems 7500 Real-Time PCR System.' Applied Biosystems, [Online] 2007, p. 1, XP008154148.
GenBank Accession No. ZMU16123, Created Dec. 16, 1995. [online], [retrieved on Oct. 6, 2010]. Retrieved from the Internet <URL:http://www.ncbi.nlm.nih.gov/nuccore/1122438>.
GenBank Accession No. AC133634, Created Nov. 22, 2002. [online], [retrieved on Oct. 6, 2010]. Retrieved from the Internet <URL: http://www.ncbi.nlm.nih.gov/nuccore/25167187>.
GenBank Accession No. DV681892, Created May 17, 2006. [online], [retrieved on Oct. 9, 2010]. Retrieved from the Internet <URL:http://www.ncbi.nlm.nih.gov/nucest/82455291>.
Zhang J et al: "Mapping quantitative trait loci for oil, starch, and protein concentrations in grain with high-oil maize by SSR markers", Euphytica, Kluwer Academic Publishers, DO, vol. 162, No. 3, Aug. 3, 2007, pp. 335-344, XP019603818, ISSN: 1573-5060.
Subhash Chander et al: "Genetic dissection of tocopherol content and composition in maize grain using quantitative trait loci analysis and the candidate gene approach", Molecular Breeding, Kluwer Academic Publishers, DO, vol. 22, No. 3, Apr. 12, 2008, pp. 353-365, XP019611834. ISSN: 1572-9788.

* cited by examiner

*Primary Examiner* — Angela M Bertagna
(74) *Attorney, Agent, or Firm* — James Daly, IV; Faegre Baker Daniels LLP

(57) ABSTRACT

This invention relates in part to detecting herbicide tolerant plants-more specifically, an aad-1 transformation event in corn plants. The subject invention also provides assays for detecting the presence of the subject event in a sample (of corn grain, for example). Kits and conditions useful in conducting the assays are also provided. The subject invention also relates in part to plant breeding using the subject methods. In some embodiments, this event/polynucleotide sequence can be "stacked" with other traits. More specifically, the invention relates in part to an endpoint Taqman PCR assay for AAD-1 corn event 40278-9. Some embodiments are directed to assays that are capable of high throughput zygosity analysis. The subject invention further relates, in part, to the use of a preferred reference gene for use in determining zygosity.

17 Claims, 3 Drawing Sheets

DETECTION OF AAD1 EVENT DAS-40278-9

CROSS REFERENCE TO RELATED APPLICATIONS

This application is a 371 national stage application of International Application No. PCT/US2010/045871, with an International Filing Date of Aug. 18, 2010, which claims priority to U.S. Application Ser. No. 61/327,366, filed Apr. 23, 2010, and to U.S. Application No. 61/235,248, filed on Aug. 19, 2009, all of which are incorporated herein by reference in their entirety.

BACKGROUND OF THE INVENTION

The aad-1 gene (originally from Sphingobium herbicidovorans) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as diclofop and quizalofop) herbicides and may be used as a selectable marker during plant transformation and in breeding nurseries. The aad-1 gene, itself, for herbicide tolerance in plants was first disclosed in WO 2005/107437 (see also US 2009-0093366).

Various methods of event detection are known. However, they each have issues. One method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an event amplicon of the present invention. Following this method, an oligonucleotide is designed which overlaps the genomic flanking and inserted DNA junction. The oligonucleotide is hybridized to single-stranded PCR product (i.e. event amplicon) from the region of interest (one primer (i.e. the first event primer) in the inserted DNA and one in the flanking genomic DNA sequence (i.e, the second event primer)) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Hydrolysis probe assay, otherwise known as TAQMAN (PE Applied Biosystems, Foster City, Calif.), is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, Taq DNA polymerase cleans and releases the fluorescent moiety away from the quenching moiety on the FRET probe. A fluorescent signal indicates the presence of the flanking/transgene insert sequence due to successful amplification and hybridization.

Another challenge, among many, is finding a suitable reference gene for a given test. For example, as stated in the abstract of Czechowski et al., "An exceptionally large set of data from Affymetrix ATH1 whole-genome GeneChip studies provided the means to identify a new generation of reference genes with very stable expression levels in the model plant species Arabidopsis (Arabidopsis thaliana). Hundreds of Arabidopsis genes were found that outperform traditional reference genes in terms of expression stability throughout development and under a range of environmental conditions." (Czechowski et al. (2005) Genome-wide identification and testing of superior reference genes for transcript normalization in Arabidopsis. Plant Physiol. 139, 5-17.)

Brodmann et al. (2002) relates to real-time quantitative PCR detection of transgenic maize content in food for four different maize varieties approved in the European Union. Brodmann, P. D., P. D., Ilg E. C., Berthoud H., and Herrmann, A. Real-Time Quantitative Polymerase Chain Reaction Methods for Four Genetically Modified Maize Varieties and Maize DNA Content in Food. J. of AOAC international 2002 85 (3)

Hernandez et al. (2004) mentions four possible genes for use with real-time PCR. Hernandez, M., Duplan, M.-N., Berthier, G., Vaitilingom, M., Hauser, W., Freyer, R., Pla, M., and Bertheau, Y. Development and comparison of four real-time polymerase chain reaction systems for specific detection and quantification of Zea mays L. J. Agric. Food Chem. 2004, 52, 4632-4637.

Costa et al. (2007) looked at these four genes (also in the real-time PCR context) and concluded that the alcohol dehydrogenase and zein genes were the best reference genes for detecting a sample "event" (a lectin gene) for transgenic feed intermix issues. Costa, L. D., and Martinelli L. Development of a Real-Time PCR Method Based on Duplo Target Plasmids for Determining an Unexpected Genetically Modified Soybean Intermix with Feed Components. J. Agric. Food Chem. 2007, 55, 1264-1273.

Huang et al. (2004) used plasmid pMulM2 as reference molecules for detection of MON810 and NK603 transgenes in maize. Huang and Pan, "Detection of Genetically Modified Maize MON810 and NK603 by Multiplex and Real-Time Polymerase Chain Reaction Methods," J. Agric. Food Chem., 2004, 52 (11), pp 3264-3268.

Gasparic et al. (2008) suggest LNA technology, from a comparison to cycling probe technology, TaqMan, and various real-time PCR chemistries, for quantitatively analyzing maize events (such as MON810). Gašparič, Cankar, Žel, and Gruden, "Comparison of different real-time PCR chemistries and their suitability for detection and quantification of genetically modified organisms," BMC Biotechnol. 2008; 8: 26.

US 20070148646 relates to a primer extension method for quantification that requires controlled dispensation of individual nucleotides that can be detected and quantified by the amount of nucleotides incorporated. This is different from the TaqMan PCR method using an internal reference gene.

To distinguish between homozygous and hemizygous genotypes of TC 1507, an Invader assay has been successfully used for this event. Gupta, M., Nirunsuksiri, W., Schulenberg, G., Hartl, T., Novak, S., Bryan, J., Vanopdorp, N., Bing, J. and Thompson, S. A non-PCR-based Invader Assay Quantitatively Detects Single-Copy Genes in Complex Plant Genomes. Mol. Breeding 2008, 21, 173-181.

Huabang (2009) relates to PCR-based zygosity testing of transgenic maize. However, no reference gene appears to be used. Huabang, "An Accurate and Rapid PCR-Based Zygosity Testing Method for Genetically Modified Maize," Molecular Plant Breeding, 2009, Vol. 7, No. 3, 619-623.

BRIEF SUMMARY OF THE INVENTION

The subject invention provides assays for detecting the presence of the AAD-1 corn event designated Yellow Dent maize hybrid seed (*Zea Mays L.*): DAS-40278-9 in a sample (of corn grain, for example). (Representative seed was deposited with American Type Culture Collection (ATCC) under Accession No. PTA-10244 (Yellow Dent maize hybrid seed (*Zea Mays L.*): DAS-40278-9; deposited in accordance with the Budapest Treaty on behalf of Dow AgroSciences LLC; date of receipt of seeds/strain(s) by the ATCC: Jul. 10, 2009, viability confirmed Aug. 17, 2009.) The address of the depository is American Type Culture Collection (ATCC). IP, Licensing, and Services, 10801 University Boulevard, Manassas, Va. 20110, U.S.A. Kits and conditions useful in conducting the assays are also provided.

More specifically, the present invention relates in part to endpoint TaqMan PCR assays for the AAD-1 event in corn utilizing a maize endogenous reference gene. Some embodiments are directed to assays that are capable of high throughput zygosity analysis. The subject invention further relates, in part, to the discovery of a preferred invertase reference gene for use in determining zygosity.

Thus, this invention also relates in part to plant breeding incorporating any of the subject detection methods. In some embodiments, said event can be "stacked" with other traits, including, for example, other herbicide tolerance gene(s) and/or insect-inhibitory proteins. The subject procedures can be used to uniquely identify corn lines comprising the event of the subject invention.

BRIEF DESCRIPTION OF THE SEQUENCES

Figure 1:
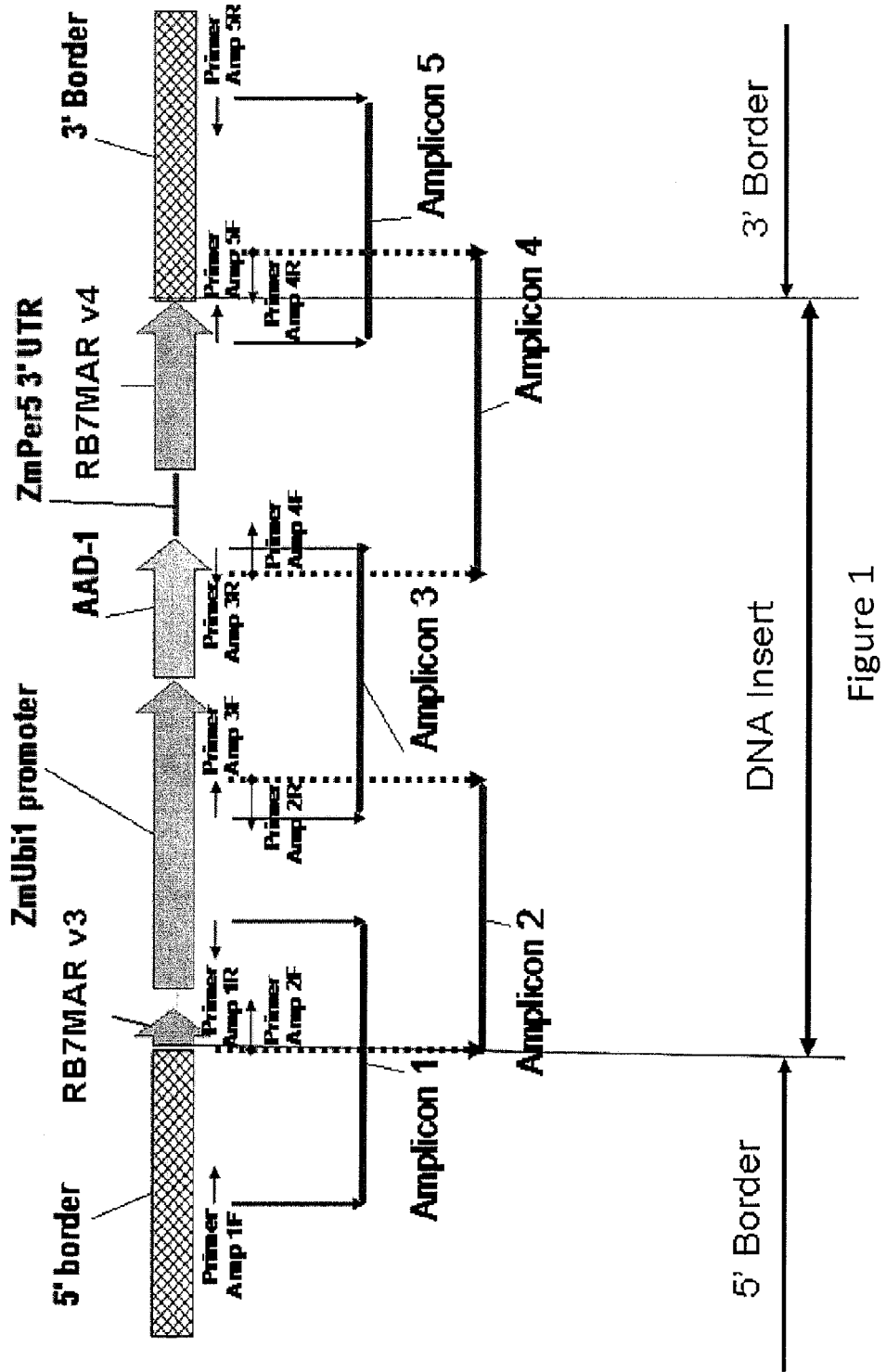
FIG. 1 shows a cloning Strategy for the DNA Insert in the Corn Event DAS-40278-9.

SEQ ID NO: 1 provides a sequence of 5' and 3' genomic flanking sequences on either side of the AAD-1 insert, including the insert, for Corn Event DAS-40278-9.

SEQ ID NOs: 2-7 are primers and probes for use according to the subject invention.

SEQ ID NO:8 is the exemplified event amplicon.

SEQ ID NO:9 is the exemplified reference amplicon.

DETAILED DESCRIPTION OF THE INVENTION

Transgenic AAD-1 (providing herbicide tolerance) corn event DAS-40278-9 was generated by Whisker-mediated transformation. Both 5' and 3' end flanking sequences of this AAD-1 transgene insert were cloned, sequenced, and characterized as detailed in U.S. Ser. No. 61/235,248 (filed on Aug. 19, 2009).

Specific TAQMAN primers and probe were designed, as detailed herein, in part according to the DNA sequences located in the 5' insert-to-plant junction. Event specificity of the primers and probe was successfully tested in duplex format with the corn invertase as a reference gene in real time PCR against 16 different AAD-1 corn events and two non-transgenic corn varieties. Procedures for end-point event specific TAQMAN assays for AAD-1 corn DAS-40278-9 were developed, as detailed herein.

The sequence spanning the region of the integration junction between host plant DNA and the integrated gene construct in this AAD-1 corn is a unique sequence. It was used to develop event specific assays (conventional PCR or realt time PCR) to detect presence of AAD-1 Corn DAS-40278-9 for GMO testing and to determine zygosity status of plants in breeding populations. The event-specific TAQMAN assay reported herein can be employed for both applications.

The subject invention provides assays for detecting the presence of the subject transgenic corn event DAS-40278-9 (also known as pDAS1740-278) in a sample. Aspects of the subject invention include methods of designing and/or producing any diagnostic nucleic acid molecules exemplified or suggested herein.

This invention also relates in part to plant breeding incorporating any of these methods. In some embodiments, the subject event can be "stacked" with other traits (such as other herbicide tolerance gene(s) and/or gene(s) that encode insect-inhibitory proteins, for example. Plant lines comprising the subject event can be detected using sequences disclosed and suggested herein.

In some embodiments, this invention relates to the identification of herbicide-tolerant corn lines. The subject invention relates in part to detecting the presence of the subject event in order to determine whether progeny of a sexual cross contain the event of interest. In addition, a method for detecting the event is included and is helpful, for example, for complying with regulations requiring the pre-market approval and labeling of foods derived from recombinant crop plants, for example.

The subject invention relates in part to a fluorescence-based endpoint TaqMan PCR assay utilizing an endogenous gene as a reference (copy number) control for high-throughput zygosity analysis of the AAD-1 maize event. The subject invention further relates, in part, to the discovery of a preferred reference gene, invertase. Several reference genes were identified as possible options.

The subject invention also relates in part to the development of a biplex endpoint TaqMan PCR for AAD-1 event specific zygosity analysis. Further, the subject invention relates in part to the development of AAD-1 breeding test kits.

Endpoint TaqMan assays are based on a plus/minus strategy, by which a "plus" signifies the sample is positive for the assayed gene and a "minus" signifies the sample is negative for the assayed gene. These assays typically utilize two sets of oligonucleotides for identifying the AAD-1 transgene sequence and the wild-type gene sequence respectively, as well as dual-labeled probes to measure the content of transgene and wild type sequence.

Although the Invader assay has been a robust technique for characterizing events, it is very sensitive to DNA quality. In addition, the assay requires a high quantity of DNA. Invader also requires an additional denaturing step which, if not handled properly, can render the Invader assay unsuccessful. Additionally, the longer assay time of the Invader assay is limited in its flexibility to efficiently handle large numbers of AAD-1 samples for analysis in a commercial setting. One main advantage of the subject invention is time savings and elimination of the denaturing step.

The subject Endpoint TaqMan analysis for detecting AAD-1 events offers surprising advantages over Invader, particularly in analyzing large number of samples.

This invention can impact the development and characterization of AAD-1 herbicide tolerance traits in crops including corn, soybean, and cotton.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR §1.822 is used. As used herein, the term "progeny" denotes the offspring of any generation of a parent plat which comprises AAD-1 corn event DAS-40278-9.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" spans the point at which DNA inserted into the genome is linked to DNA from the corn native genome flanking the insertion point. Included are the DNA sequences that span the insertions in herein-described corn events and similar lengths of flanking DNA.

The subject invention relates to the identification of the subject event. Related PCR primers and amplicons are included in the invention. These molecules can be used to detect or identify commercialized transgenic corn varieties or lines derived from the subject transgenic corn lines.

The entire sequence of the insert, together with portions of the respective flanking sequences, are provided herein as SEQ ID NO:1. The coordinates of the insert and flanking sequences for this event with respect to SEQ ID NO:1 (8557 basepairs total) are printed below.

|  | 5' Flanking | Insert | 3'Flanking |
| --- | --- | --- | --- |
| residue #s (SEQ: 1): | 1-1873 | 1874-6689 | 6690-8557 |
| length (bp): | 1873 bp | 4816 bp | 1868 bp |

Figure 2:
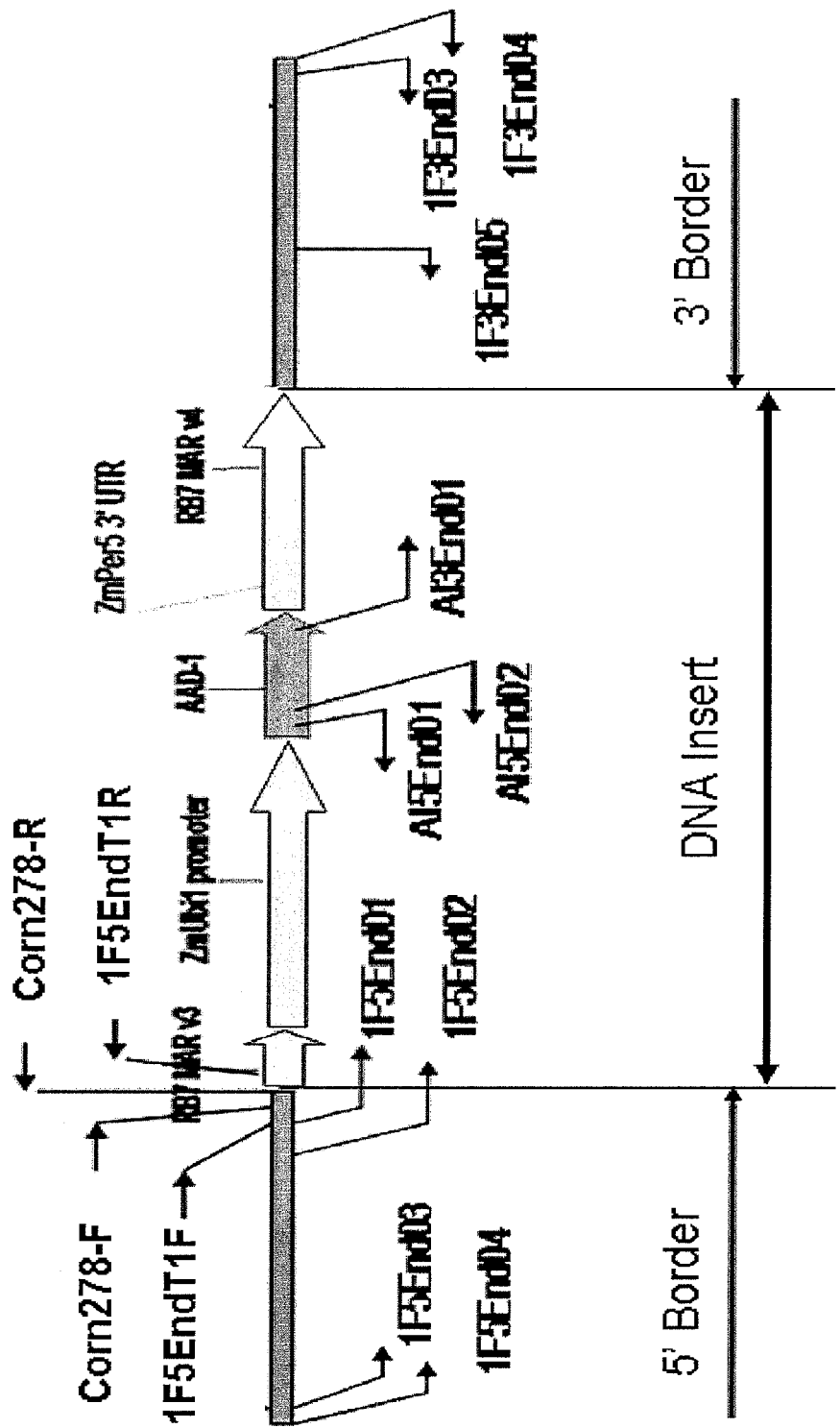
FIG. 2 is a diagram of the Primers Used in PCR Amplification for Confirmation of Flanking Border Regions of the Corn Event DAS-40278-9 The schematic diagram depicts the primer locations for confirming the full length sequencing of the AAD-1 corn event DAS-40278-9 from 5' to 3' borders.
Figure 3:
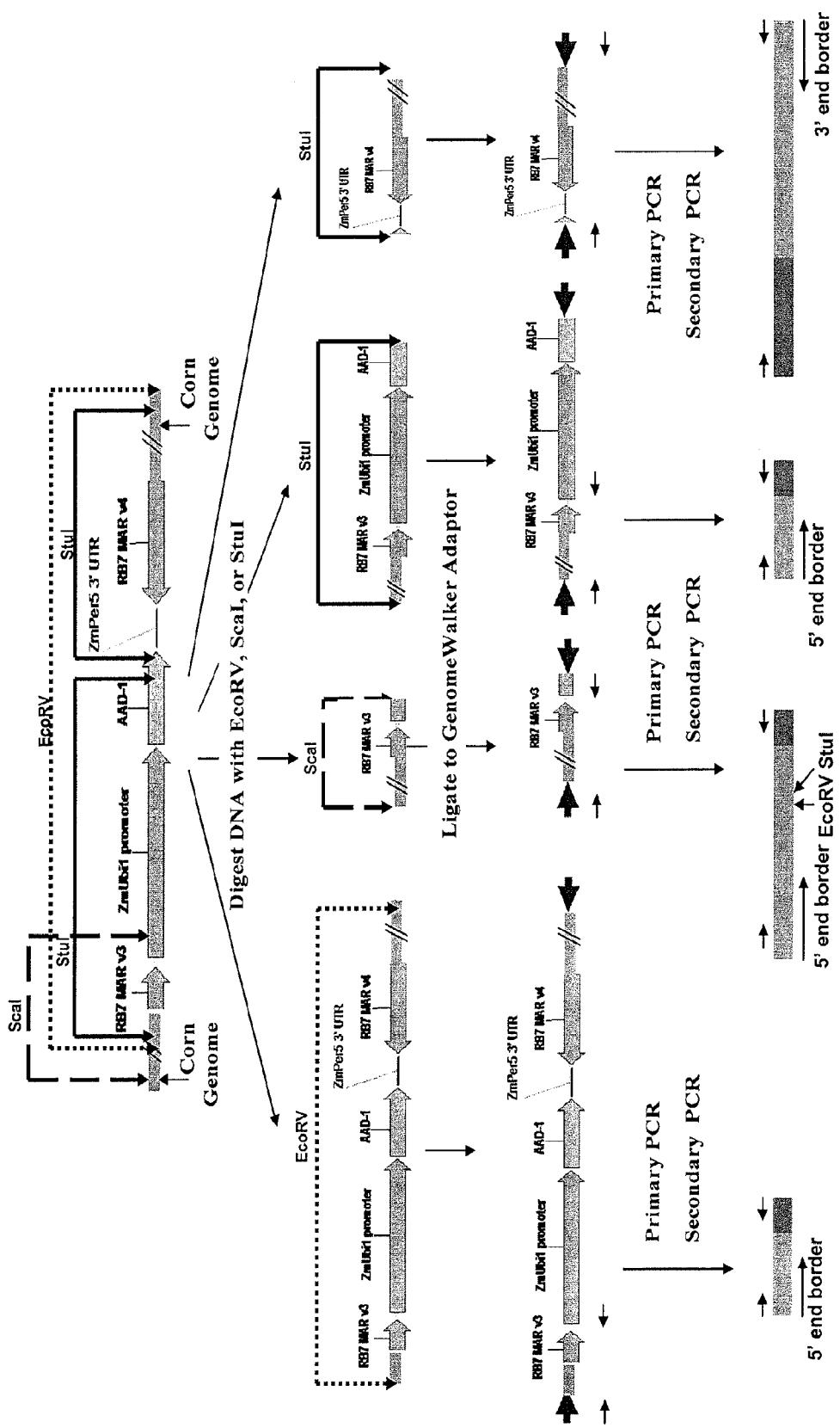
FIG. 3 shows a cloning Strategy for the Flanking Border Sequences from the Corn Event DAS-40278-9 Genomic DNA of the Corn Event DAS-40278-9 was digested with EcoR V, Stu I, or Sca I and generated corresponding GenomeWalker™ libraries, which were used as templates to amplify the target DNA sequences.

The components of the AAD-1 insert and flanking sequences for this event are further illustrated in FIGS. 1 through 3.

Detection techniques of the subject invention can be used in conjunction with plant breeding, to determine which progeny plants comprise a given event, after a parent plant comprising an event of interest is crossed with another plant line in an effort to impart one or more additional traits of interest in the progeny. The subject methods are useful in, for example, corn breeding programs as well as quality control, especially for commercialized transgenic cornseeds. This can also benefit product registration and product stewardship. These methods can be used for accelerated breeding strategies.

In some embodiments, the fluorescence-based end-point TaqMan assay for zygosity analysis allows the results to be directly read in a plate reader for identification of the AAD-1 event in corn and the reference gene.

The subject invention includes breeding applications such as testing the introgression of the AAD-1 event into other corn lines.

Detection methods and kits of the subject invention can be used to identify events according to the subject invention. Methods and kits of the subject invention can be used for accelerated breeding strategies and to establish linkage data.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These Taqman PCR analysis methods benefit maize breeding programs as well as quality control, especially for commercialized transgenic maize seeds. Taqman PCR detection kits for these transgenic maize lines can also now be made and used. This can also benefit product registration and product stewardship.

Still further, subject methods can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

As used herein, the term "corn" means maize (*Zea mays*) and includes all varieties thereof that can be bred with corn.

This invention further includes processes of making crosses and using methods of the subject invention. For example, the subject invention includes a method for producing an $F_1$ hybrid seed by crossing an exemplified plant with a different (e.g. in-bred parent) plant, harvesting the resultant hybrid seed, and detecting for the subject event. Characteristics of the resulting plants may also be improved by incorporating methods of the subject invention.

A herbicide-tolerant corn plant can be bred by first sexually crossing a first parental corn plant consisting of a corn plant grown from seed of a line referred to herein, and a second parental corn plant, thereby producing a plurality of first progeny plants; and then selecting a first progeny plant that is resistant to a herbicide (or that possesses a subject event); and selfing the first progeny plant, thereby producing a plurality of second progeny plants; and then selecting from the second progeny plants a plant that is resistant to a herbicide (or that possesses at least one of the events). These steps can further include the back-crossing of the first progeny plant or the second progeny plant to the second parental corn plant or a third parental corn plant. A corn crop comprising corn seeds of the subject invention, or progeny thereof, can then be planted.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (back-crossed) to the recurrent parent. The resulting parent is expected to have the attributes of the recurrent parent (e.g., cultivar) and the desirable trait transferred from the donor parent.

The present invention can be used in conjunction with a marker assisted breeding (MAB) method. Likewise, DNA molecules of the present invention can be used with other methods (such as, AFLP markers, RFLP markers, RAPD markers, SNPs, and SSRs) that identify genetically linked agronomically useful traits. The herbicide-resistance trait can be tracked in the progeny of a cross (or progeny thereof and any other corn cultivar or variety) using the MAB methods. The methods of the present invention can be used to identify any corn variety having the subject event.

Methods of the subject invention include a method of producing a herbicide-tolerant corn plant wherein said method comprises breeding with a plant having a subject event. Preferred methods further comprise selecting progeny of said cross by analyzing said progeny for an event detectable according to the subject invention. For example, the subject invention can be used to track the subject event through breeding cycles with plants comprising other desirable traits, such as agronomic traits. Plants comprising the subject event and the desired trait can be detected, identified, selected, and quickly used in further rounds of breeding, for example. The subject event/trait can also be combined through breeding, and tracked according to the subject invention, with an insect resistant trait(s) and/or with further herbicide tolerance traits. One preferred embodiment of the latter is a plant comprising the subject event combined with a gene encoding resistance to an imidazolinone herbicide, glyphosate, and/or glufosinate. A dicamba tolerance gene can be used in some embodiments.

Thus, the subject invention can be combined with, for example, traits encoding glyphosate resistance (e.g., resistant plant or bacterial EPSPS, GOX, GAT), glufosinate resistance (e.g., Pat, bar), acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries [Csr1, SurA, et al.]), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes.

Regarding additional herbicides, some additional preferred ALS (also known as AHAS) inhibitors include the triazolopyrimidine sulfonanilides (such as cloransulam-methyl, diclosulam, florasulam, flumetsulam, metosulam, and penoxsulam), pyrimidinylthiobenzoates (such as bispyribac and pyrithiobac), and flucarbazone. Some preferred HPPD inhibitors include mesotrione, isoxaflutole, and sulcotrione. Some preferred PPO inhibitors include flumiclorac, flumioxazin, flufenpyr, pyraflufen, fluthiacet, butafenacil, carfentrazone, sulfentrazone, and the diphenylethers (such as acifluorfen, fomesafen, lactofen, and oxyfluorfen).

Additionally, AAD-1 alone or stacked with one or more additional HTC traits can be stacked with one or more additional input (e.g., insect resistance, fungal resistance, or stress tolerance, et al.) or output (e.g., increased yield, improved oil profile, improved fiber quality, et al.) traits. Thus, the subject invention can be used to provide a complete agronomic package of improved crop quality with the ability to flexibly and cost effectively control any number of agronomic pests.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner.

"Commercial Utility" is defined as having good plant vigor and high fertility, such that the crop can be produced by farmers using conventional farming equipment, and the oil with the described components can be extracted from the seed using conventional crushing and extraction equipment. To be commercially useful, the yield, as measured by seed weight, oil content, and total oil produced per acre, is within 15% of the average yield of an otherwise comparable commercial maize variety without the premium value traits grown in the same region.

"Agronomically elite" means that a line has desirable agronomic characteristics such as yield, maturity, disease resistance, and the like, in addition to insect resistance due to the subject event(s). Agronomic traits, taken individually or in any combination.

As one skilled in the art will recognize in light of this disclosure, preferred embodiments of detection kits, for example, can include probes and/or primers. For example, this includes a polynucleotide probes, primers, and/or amplicons as indicated herein.

One skilled in the art will also recognize that primers and probes can be designed to hybridize, under a range of standard hybridization and/or PCR conditions, to a segment of SEQ ID NO:1 (or the complement), and complements thereof, wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

The components of each of the "inserts" are illustrated in FIGS. 1 through 3. The DNA polynucleotide sequences of these components, or fragments thereof, can be used as DNA primers or probes in the methods of the present invention.

In some embodiments of the invention, compositions and methods are provided for detecting the presence of the transgene/genomic insertion region, in plants and seeds and the like, from a corn plant.

In some embodiments, DNA sequences that comprise a contiguous fragment of the novel transgene/genomic insertion region are an aspect of this invention. Included are DNA sequences that comprise a sufficient length of polynucleotides of transgene insert sequence and a sufficient length of polynucleotides of corn genomic sequence and/or sequences that are useful as primer sequences for the production of an amplicon product diagnostic for one or more of these corn plants.

Related embodiments pertain to DNA sequences that comprise at least 2, 3, 4, 5, 6, 7, 8, 9, 10, 11, 12, 13, 14, 15, 16, 17, 18, 19, 20, 21, 22, 23, 24, 25, or more contiguous nucleotides of a transgene portion of a DNA sequence identified herein, or complements thereof. Such sequences can be useful as DNA primers in DNA amplification methods. The amplicons produced using these primers are diagnostic for the corn event referred to herein. Therefore, the invention also includes amplicons and amplicons produced by such DNA primers and homologous primers.

This invention includes methods of detecting the presence of DNA, in a sample, that corresponds to the corn event referred to herein. Such methods can comprise: (a) contacting the sample comprising DNA with a primer set that, when used in a nucleic acid amplification reaction with DNA from at least one of these corn events, produces an amplicon that is diagnostic for said event(s); (b) performing a nucleic acid amplification reaction, thereby producing the amplicon; and (c) detecting the amplicon.

Further detection methods of the subject invention include a method of detecting the presence of a DNA, in a sample, corresponding to at least one of said events, wherein said method comprises: (a) contacting the sample comprising DNA with a probe that hybridizes under stringent hybridization conditions with DNA from at least one of said corn events and which does not hybridize under the stringent hybridization conditions with a control corn plant (non-event-of-interest DNA); (b) subjecting the sample and probe to stringent hybridization conditions; and (c) detecting hybridization of the probe to the DNA.

This invention includes methods of detecting the presence of DNA, in a sample, from at least one of the maize plants referred to herein. Such methods can comprise: (a) contacting the sample comprising DNA with a primer set that, when used in a nucleic acid amplification reaction, of the subject invention, with DNA from at least one of these maize events; (b) performing a TAQMAN PCR amplification reaction using a reference gene identified herein; and (c) analyzing the results.

In still further embodiments, the subject invention includes methods of producing a corn plant comprising the AAD-1 event of the subject invention, wherein said method comprises the steps of: (a) sexually crossing a first parental corn line (comprising an expression cassettes of the present invention, which confers said herbicideresistance trait to plants of said line) and a second parental corn line (that lacks this herbicide tolerance trait) thereby producing a plurality of progeny plants; and (b) selecting a progeny plant by the use of molecular markers. Such methods may optionally comprise the further step of back-crossing the progeny plant to the second parental corn line to producing a true-breeding corn plant that comprises said herbicide tolerance trait.

According to another aspect of the invention, methods of determining the zygosity of progeny of a cross involving the subject event are provided. Said methods can comprise contacting a sample, comprising corn DNA, with a primer set of the subject invention. Said primers, when used in a nucleic-acid amplification reaction with genomic DNA from at least one of said corn events, produce a first amplicon that is diagnostic for at least one of said corn events. Such methods further comprise performing a nucleic acid amplification reaction, thereby producing the first amplicon; detecting the first amplicon; and contacting the sample comprising corn DNA with said primer set, when used in a nucleic-acid amplification reaction with genomic DNA from corn plants, produces a second amplicon comprising the native corn genomic DNA homologous to the corn genomic region; and performing a nucleic acid amplification reaction, thereby producing the second amplicon. The methods further comprise detecting the second amplicon, and comparing the first and second amplicons in a sample, wherein the presence of both amplicons indicates that the sample is heterozygous for the transgene insertion.

DNA detection kits can be developed using the compositions disclosed herein and methods well known in the art of DNA detection. The kits are useful for identification of the subject corn event DNA in a sample and can be applied to methods for breeding corn plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule which is attached to a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said corn events, whether from a corn plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated/synthesized nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a nucleic acid molecule of the present invention has the nucleic acid sequence set forth in SEQ ID NOS:2-7, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the corn plant resulting from a sexual cross contains transgenic event genomic DNA from the corn plant of the present invention, DNA extracted from a corn plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject corn event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

All patents, patent applications, provisional applications, and publications referred to or cited herein are incorporated by reference in their entirety to the extent they are not inconsistent with the explicit teachings of this specification.

The following abbreviations are used unless otherwise indicated.

AAD-1 aryloxyalkanoate dioxygenase-1
bp base pair
° C. degrees Celcius
DNA deoxyribonucleic acid
DIG digoxigenin
EDTA ethylenediaminetetraacetic acid
kb kilobase
μg microgram
μL microliter
mL milliliter
M molar mass
OLP overlapping probe
PCR polymerase chain reaction
PTU plant transcription unit
SDS sodium dodecyl sulfate
SOP standard operating procedure
SSC a buffer solution containing a mixture of sodium chloride and sodium citrate, pH 7.0
TBE a buffer solution containing a mixture of Tris base, boric acid and EDTA, pH 8.3
V volts

EXAMPLES

Example 1

Event Specific Taqman Assay

An event specific Taqman assay was developed to detect the presence of maize event DAS-40278-9 and to determine zygosity status of plants in breeding populations. To develop an event specific assay, specific Taqman primers and probes were designed according to the DNA sequences located in the 5' insert-to-plant junction. For specific detection of DAS-40278-9, a 73-bp DNA fragment that spans this 5'-integration junction was amplified using two specific primers. The amplification of this PCR product was measured by a target-specific MGB probe synthesized by Applied Biosystems containing the FAM reporter at its 5'end. Specificity of this Taqman detection method for AAD-1 corn event DAS-40278-9 was tested against 16 different AAD-1 corn events and non-transgenic corn variety in duplex format with the corn specific endogenous reference gene, Invertase.

Example 1.1 gDNA Isolation gDNA samples of 16 different AAD-1 corn events and non-transgenic corn varieties were tested in this study. gDNA was extracted with two approaches, Qiagen kit or CTAB. For the gDNA samples extracted with the Qiagen kit, eight corn fresh leaf discs were used for gDNA extraction according to a modified Qiagen DNeasy 96 Plant Kit protocol. For the gDNA samples extracted by using CTAB procedure, about 0.3 g lyophilized leaf tissue was used following a protocol from Permingeat et al., 1998. gDNA was quantified with the Pico Green method according to vendor's instructions (Molecular Probes, Eugene, Oreg.). The gDNA samples were diluted with DNase-free water resulting in a concentration of 10 ng/μL for the purpose of this study.

Example 1.2

Taqman Assay and Results

Specific Taqman primers and probes were designed for the DAS-40278-9 event specific Taqman assay. These reagents can be used with the conditions listed below to detect AAD-1 corn event DAS-40278-9. Table 1 lists the primer and probe sequences that were developed specifically for the detection of event DAS-40278-9.

TABLE 1

PCR Primers and Probes

| Name | Description | 5' to 3' sequence |
| --- | --- | --- |
| Event Target Reaction | | |
| Corn278-F | Forward Primer | Seq ID NO: 2:<br>5'- ATTCTGGCTTTGCTGTAAATCGT-3' |
| Corn278-R | Reverse Primer | Seq ID NO: 3:<br>5'- TTACAATCAACAGCACCGTACCTT-3' |
| Corn278-Probe | Probe | Seq ID NO: 4:<br>5'- FAM- CTAACCTTCATTGTATTCC-MGB- 3' |
| Invertase Reference System Reaction | | |
| IVF | Forward Primer | Seq ID NO: 5:<br>5'- TGGCGGACGACGACTTGT -3' |
| IVR | Reverse Primer | Seq ID NO: 6:<br>5'- AAAGTTTGGAGGCTGCCGT -3' |
| IV-Probe | Probe | Seq ID NO: 7:<br>5'- HEX-CGAGCAGACCGCCGTGTACTTCTACC-BHQ2 -3' |

The multiplex PCR conditions for amplification are as follows: 1×PCR buffer, 0.5-2.5 mM $MgCl_2$, 0.2 mM dNTP, 0.2 μM Primer Corn-278-F, 0.2 μM Primer Corn-278-R, 0.2 μM Primer_IV-F, 0.2 μM Primer_IV-R, 0.08 μM Probe_Corn-278-Probe, 0.08 uM Probe_IV-probe, 40 U/mL Hot-Start Taq, 0.6 to 2.4 ug/mL DNA in a total reaction of 25 μl. Various concentrations of $MgCl_2$ and DNA were tested. Concentrations of 0.5 mM, 1.0 mM, 1.8 mM, and 2.5 mM of $MgCl_2$ were used. The cocktail was amplified using the following conditions: i) 95° C. for 15 min., ii) 95° C. for 20 sec, iii) 60° C. for 60 sec, iv) repeat step ii-iii for 50 cycles, v) 4° C. hold. The Real time PCR was carried out on Bio-rad iCycler™ system. Data analysis was based on measurement of the cycle threshold (CT), which is the PCR cycle number when the fluorescence measurement reaches a set value. CT value was calculated automatically by iCycler software.

The amplicon sequences generated using the above primers were as follows:

278F and 278R:

(SEQ ID NO: 8)

ttacaatcaacagcaccgtaccttgaagcggaatacaatgaaggttagctacgatttacagcaaagccagaat

IVF and IVR:

(SEQ ID NO: 9)

tggcggacgacgacttgtccgagcagaccgccgtgtacttctacctgctcaagggcacggacggcagcctccaaacttt

The Taqman detection method for AAD-1 corn event DAS-40278-9 was tested against 16 different AAD-1 corn events and non-transgenic corn variety in duplex format with corn specific endogenous Invertase as a reference gene. This assay specifically detected the AAD-1 corn event DAS-40278-9 and did not produce or amplify any false-positive results from the controls (i.e. the 16 different AAD-1 corn events and non-transgenic corn varieties). The event specific primers and probes can be used for the detection of the AAD-1 corn event DAS-40278-9 and these conditions and reagents are applicable for zygosity assays.

The invention claimed is:

1. A method for determining zygosity of a corn plant comprising an AAD-1 corn event DAS-40278-9 comprising SEQ ID NO:1, said event comprising a transgene construct comprising an AAD-1 gene, said transgene construct being flanked by a 5' flanking corn genomic DNA and a 3' flanking corn genomic DNA, said method comprising:

obtaining a DNA sample of genomic DNA from said corn plant;

producing a contacted sample by contacting said DNA sample with a. a first event primer and a second event primer, wherein said first event primer specifically binds said transgene construct, said second event primer specifically binds said 5' corn genomic flanking DNA or said 3' corn genomic flanking DNA, and wherein said first event primer and said second event primer produce an event amplicon when subjected to quantitative PCR conditions b. a reference gene forward primer and a reference gene reverse primer that produce a reference gene amplicon from an endogenous corn reference gene when subjected to quantitative PCR conditions c. a florescent event probe that hybridizes with said event amplicon d. a florescent reference gene probe that hybridizes with said reference amplicon;

subjecting said contacted sample to fluorescence-based endpoint quantitative PCR conditions;

quantitating said florescent event probe that hybridized to said event amplicon;

quantitating said florescent reference probe that hybridized to said reference amplicon;

comparing amounts of hybridized florescent event probe to hybridized florescent reference probe; and determining zygosity of said corn plant comprising event DAS-40278-9 by comparing florescence ratios of hybridized fluorescent event probe and hybridized fluorescent reference probe.

2. The method of claim 1 wherein said event or reference amplicon consists of 50-100 residues.

3. The method of claim 1 wherein said reference gene is an endogenous *Zea mays* invertase gene.

4. The method of claim 1 wherein said second event primer binds to the complement of a segment of residues 1673-1873 of SEQ ID NO: 1.

5. The method of claim 1 wherein said second event primer binds to a segment of residues 6690-6890 of SEQ ID NO:1.

6. The method of claim 1 wherein said event amplicon is 73 basepairs.

7. The method of claim 1 wherein said reference gene primer comprises a sequence selected from the group consisting of SEQ ID NO: 5 and SEQ ID NO: 6.

8. The method of claim 1 wherein said reference gene forward and reverse primers comprise SEQ ID NO: 5 and SEQ ID NO:6, and said fluorescent reference gene probe comprises SEQ ID NO:7.

9. The method of claim 1 wherein said probes are labeled with a fluorescent dye and quencher.

10. The method of claim 9 wherein said event probe comprises 6-fluorescein amidite at the 5' end of said event probe and a minor groove binder quencher on the 3' end of said event probe.

11. The method of claim 1 wherein said reference amplicon is a 79 basepair fragment amplified by said reference primers.

12. The method of claim 9 wherein said reference probe is labeled with Hexachloro-Fluorescein at the 5' end of said reference probe and a dark quencher at the 3' end of said reference probe.

13. The method of claim 1 wherein said event amplicon consists of SEQ ID NO:8 and said reference amplicon consists of SEQ ID NO:9.

14. The method of claim 1 wherein said fluorescent event probe comprises SEQ ID NO:4.

15. The method of claim 1 wherein said event primers are SEQ ID NO: 2 and SEQ ID NO: 3.

16. The method of claim 1 wherein results of said method are read directly in a plate reader.

17. A kit for performing the method of claim 1, said kit comprising said first event primer, said second event primer, said reference forward primer, said reference reverse primer, said event probe, and said reference probe, wherein said event primers consist of SEQ ID NO:2 and SEQ ID NO:3, said reference primers consist of SEQ ID NO:5 and SEQ ID NO:6, said event probe consists of SEQ ID NO:4, and said reference probe consists of SEQ ID NO:7.

* * * * *

SEQUENCE LISTING

<160> NUMBER OF SEQ ID NOS: 9

<210> SEQ ID NO 1
<211> LENGTH: 8557
<212> TYPE: DNA
<213> ORGANISM: Artificial Sequence
<220> FEATURE:
<223> OTHER INFORMATION: AAD-1 insert and flanking sequences

<400> SEQUENCE: 1

| | | | | | |
|---|---|---|---|---|---|
| actggtattt | aatatacttt | aataaatatt | attagattcc | tcgtcaaaga | acttttaca | 60 |
| atatatctat | ttagaatcat | atatgtcata | gttttttttc | taagagtcta | gtttactagt | 120 |
| aaaatccgac | tcacattttt | cgaacttggg | atgcaacact | taaatagtac | aaaaccttgg | 180 |
| tatgcagtat | tttacattgt | aagattcaaa | atttctaaag | cagtatatat | atgtttccag | 240 |
| aaacttatag | atatagaaaa | aacagagaga | cgtatgcgaa | aattcgataa | aggtgtacat | 300 |
| tggattcgca | aggctaaata | catatttatc | gtggatccat | gcagagtttg | ggtaataaaa | 360 |
| ttagatactt | ccaatcatgt | gccacataat | cacgtaacat | tagtaattta | aatgacatta | 420 |
| ccatgtccaa | ctgatttaaa | acacaaactc | ttcttgaacc | atatagtttg | acaaaccaaa | 480 |
| tatatataac | tggagctact | agttatgaat | caattaaaaa | ttactttgaa | gattcaacgt | 540 |
| agtgccagtt | tggctctagc | acatctaacc | agaagggcta | aggctggctt | caacaggaac | 600 |
| agccaaatcc | gagatcgagc | catttgccat | ttttgggtag | ttagtttaac | tttcatatat | 660 |
| cttcccatcc | ttttttgcct | agcctaaatg | gctttgatgt | tgaagaccat | attaatttgc | 720 |
| ttcagtggca | ctaggacaac | catattggct | ttggctgacc | cgttagagtt | agcctaatgg | 780 |
| gtggaagggg | agggaagggg | aggatcgatg | gtggcatgag | agaggggttg | acgatcacga | 840 |
| tgatgatgcg | agtgaggagg | agaggtggc | gacgacacag | gggagaaagg | agagggacgc | 900 |
| taggagcgtc | aagggcgtgg | gggagggag | ggtcggaggg | atgaaggatg | acctaaatat | 960 |
| tattgttgag | tgatagaggg | ttattcaact | atccgacccg | tcgattttga | tggtatgtta | 1020 |
| aatttgtgtg | tcatttgttt | gatggattta | gtaaaggtta | tgggtctaga | ggtgattttt | 1080 |
| gttgggtggg | ttttacagag | tttaaactag | cggattatat | agtggtatag | aagatatagt | 1140 |
| tttattagaa | catctccaaa | atgtgactcg | aaataatacc | cccaaaattt | aaaatactac | 1200 |
| atcattttga | taaaaaaggt | aaagtagagc | actgttggaa | cagtttttaa | aagttgtgcc | 1260 |
| ctatatttta | aaatagggta | ctgatttaaa | atattgttgt | ggggatagaa | tatccccggg | 1320 |
| tccactagaa | ggcgagaagg | cctcgcgtgt | ggccacgggc | cagttacccc | gcaaggccat | 1380 |
| cccttcgtgg | gtcgagctag | aattactggt | agaatgggct | gaccgaagaa | ggcaacagac | 1440 |

```
tcgagcccaa acaatccatc ggctcgtgcg ctatccacag aaactacccg actttccggc    1500
gcatggcatc ctagaatatc ggggcgtatt agggatgagt cagcgagatt ttcggaagat    1560
tagttcagtt tgttcgctat tatttaggag acatatgatc ctcatgtacg tatggagtgc    1620
cccacggtcg tgtatataag gtccagaggg tacccccatca tttctatcga ccatctacct    1680
atctcatcag cttttctcca ttcaggagac ctcgcttgta acccaccaca tatagatcca    1740
tcccaagaag tagtgtatta cgcctctcta agcggcccaa acttgcagaa aaccgcctat    1800
ccctctctcg tgcgtccagc acgaaccatt gagttacaat caacagcacc gtaccttgaa    1860
gcggaataca atgaaggtta gctacgattt acagcaaagc cagaatacaa tgaaccataa    1920
agtgattgaa gctcgaaata tacgaaggaa caaatatttt taaaaaaata cgcaatgact    1980
tggaacaaaa gaaagtgata tattttttgt tcttaaacaa gcatcccctc taaagaatgg    2040
cagttttcct ttgcatgtaa ctattatgct cccttcgtta caaaaatttt ggactactat    2100
tgggaacttc ttctgaaaat agtggccacc gcttaattaa ggcgcgccat gcccgggcaa    2160
gcggccgctt aattaaattt aaatgtttaa actaggaaat ccaagcttgc atgcctgcag    2220
atccccgggg atcctctaga gtcgacctgc agtgcagcgt gacccggtcg tgcccctctc    2280
tagagataat gagcattgca tgtctaagtt ataaaaaatt accacatatt ttttttgtca    2340
cacttgtttg aagtgcagtt tatctatctt tatacatata tttaaacttt actctacgaa    2400
taatataatc tatagtacta caataatatc agtgttttag agaatcatat aaatgaacag    2460
ttagacatgg tctaaaggac aattgagtat tttgacaaca ggactctaca gttttatctt    2520
tttagtgtgc atgtgttctc cttttttttt gcaaatagct tcacctatat aatacttcat    2580
ccatttattt agtacatcca tttagggttt agggttaatg gttttatag actaattttt    2640
ttagtacatc tattttattc tattttagcc tctaaattaa gaaaactaaa actctatttt    2700
agttttttta tttaatagtt tagatataaa atagaataaa ataaagtgac taaaaattaa    2760
acaaataccc tttaagaaat taaaaaaact aaggaaacat ttttcttgtt tcgagtagat    2820
aatgccagcc tgttaaacgc cgtcgacgag tctaacggac accaaccagc gaaccagcag    2880
cgtcgcgtcg ggccaagcga agcagacggc acggcatctc tgtcgctgcc tctggacccc    2940
tctcgagagt tccgctccac cgttggactt gctccgctgt cggcatccag aaattgcgtg    3000
gcggagcggc agacgtgagc cggcacggca ggcggcctcc tcctcctctc acggcaccgg    3060
cagctacggg ggattccttt cccaccgctc cttcgctttc ccttcctcgc ccgccgtaat    3120
aaatagacac cccctccaca ccctctttcc caacctcgt gttgttcgga gcgcacacac    3180
acacaaccag atctcccccca aatccacccg tcggcacctc cgcttcaagg tacgccgctc    3240
gtcctccccc ccccccccc tctctacctt ctctagatcg gcgttccggt ccatgcatgg    3300
ttagggcccg gtagttctac ttctgttcat gtttgtgtta gatccgtgtt tgtgttagat    3360
ccgtgctgct agcgttcgta cacggatgcg acctgtacgt cagacacgtt ctgattgcta    3420
acttgccagt gtttctcttt ggggaatcct gggatggctc tagccgttcc gcagacggga    3480
tcgatttcat gattttttttt gtttcgttgc atagggtttg gtttgccctt ttcctttatt    3540
tcaatatatg ccgtgcactt gtttgtcggg tcatctttc atgcttttttt ttgtcttggt    3600
tgtgatgatg tggtctggtt gggcggtcgt tctagatcgg agtagaattc tgtttcaaac    3660
tacctggtgg atttattaat tttggatctg tatgtgtgtg ccatacatat tcatagttac    3720
gaattgaaga tgatggatgg aaatatcgat ctaggatagg tatacatgtt gatgcgggtt    3780
ttactgatgc atatacagag atgctttttg ttcgcttggt tgtgatgatg tggtgtggtt    3840
```

```
gggcggtcgt tcattcgttc tagatcggag tagaatactg tttcaaacta cctggtgtat    3900
ttattaattt tggaactgta tgtgtgtgtc atacatcttc atagttacga gtttaagatg    3960
gatggaaata tcgatctagg ataggtatac atgttgatgt gggtttact gatgcatata     4020 catgatggca tatgcagcat ctattcatat gctctaacct tgagtaccta tctattataa    4080
taaacaagta tgttttataa ttatttcgat cttgatatac ttggatgatg gcatatgcag    4140
cagctatatg tggattttt tagccctgcc ttcatacgct attatttgc ttggtactgt      4200 ttcttttgtc gatgctcacc ctgttgtttg gtgttacttc tgcagggtac ccccggggtc    4260
gaccatggct catgctgccc tcagccctct ctcccaacgc tttgagagaa tagctgtcca    4320
gccactcact ggtgtccttg gtgctgagat cactggagtg gacttgaggg aaccacttga    4380
tgacagcacc tggaatgaga tattggatgc cttccacact taccaagtca tctactttcc    4440
tggccaagca atcaccaatg agcagcacat tgcattctca agaaggtttg gaccagttga    4500
tccagtgcct cttctcaaga gcattgaagg ctatccagag gttcagatga tccgcagaga    4560
agccaatgag tctggaaggg tgattggtga tgactggcac acagactcca ctttccttga    4620
tgcacctcca gctgctgttg tgatgagggc catagatgtt cctgagcatg gcggagacac    4680
tgggttcctt tcaatgtaca cagcttggga gaccttgtct ccaaccatgc aagccaccat    4740
cgaagggctc aacgttgtgc actctgccac acgtgtgttc ggttccctct accaagcaca    4800
gaaccgtcgc ttcagcaaca cctcagtcaa ggtgatggat gttgatgctg gtgacagaga    4860
gacagtccat cccttggttg tgactcatcc tggctctgga aggaaaggcc tttatgtgaa    4920
tcaagtctac tgtcagagaa ttgagggcat gacagatgca gaatcaaagc cattgcttca    4980
gttcctctat gagcatgcca ccagatttga cttcacttgc cgtgtgaggt ggaagaaaga    5040
ccaagtcctt gtctgggaca acttgtgcac catgcaccgt gctgttcctg actatgctgg    5100
caagttcaga tacttgactc gcaccacagt tggtggagtt aggcctgccc gctgagtagt    5160
tagcttaatc acctagagct cgtttaaact gagggcactg aagtcgcttg acgtgctgaa    5220
ttgtttgtga tgttggtggc gtattttgtt taaataagta agcatggctg tgattttatc    5280
atatgatcga tctttggggt tttatttaac acattgtaaa atgtgtatct attaataact    5340
caatgtataa gatgtgttca ttcttcggtt gccatagatc tgcttatttg acctgtgatg    5400
ttttgactcc aaaaaccaaa atcacaactc aataaaactca tggaatatgt ccacctgttt    5460
cttgaagagt tcatctacca ttccagttgg catttatcag tgttgcagcg gcgctgtgct    5520
ttgtaacata acaattgtta cggcatatat ccaatagcgg ccggcctcct gcagggttta    5580
aacttgccgt ggcctatttt cagaagaagt tcccaatagt agtccaaaat ttttgtaacg    5640
aagggagcat aatagttaca tgcaaaggaa aactgccatt ctttagaggg gatgcttgtt    5700
taagaacaaa aaatatatca ctttcttttg ttccaagtca ttgcgtattt ttttaaaaat    5760
atttgttcct tcgtatattt cgagcttcaa tcactttatg gttctttgta ttctggcttt    5820
gctgtaaatc gtagctaacc ttcttcctag cagaaattat taatacttgg gatattttt    5880 tagaatcaag taaattacat attaccacca catcgagctg cttttaaatt catattacag    5940
ccatataggc ttgattcatt ttgcaaaatt tccaggatat tgcaacgtt aacttaataa     6000 tatcttgaaa tattaaagct attatgatta ggggtgcaaa tggaccgagt tggttcggtt    6060
tatatcaaaa tcaaaccaaa ccaactatat cggtttggat tggttcggtt ttgccgggtt    6120
ttcagcattt tctggttttt ttttgttag atgaatatta tttaatcttt actttgtcaa     6180
```

```
atttttgata agtaaatata tgtgttagta aaaattaatt tttttacaa acatatgatc      6240 tattaaaata ttcttatagg agaatttct taataacaca tgatatttat ttattttagt      6300
cgtttgacta attttcgtt gatgtacact ttcaaagtta accaaattta gtaattaagt      6360
ataaaaatca atatgatacc taaataatga tatgttctat ttaattttaa attatcgaaa      6420
tttcacttca aattcgaaaa agatatataa gaattttgat agattttgac atatgaatat      6480
ggaagaacaa agagattgac gcattttagt aacacttgat aagaaagtga tcgtacaacc      6540
aattatttaa agttaataaa aatggagcac ttcatattta acgaaatatt acatgccaga      6600
agagtcgcaa atatttctag atattttta aagaaaattc tataaaagt cttaaaggca      6660 tatatataaa aactatatat ttatatttt tacccaaaag caccgcaagg ggtagccctg       6720
ggtgtgcgga cggactctaa acaccgacag ctggcgcgcc aggtaggggg tgtgtctttg      6780
atctgagcta gctcaatgac cattacctcc aaatgcaaga tcgcccttcg ccccgggact      6840
atgttttgct ttggaaccat ctcatccata gcagatgaag agggaactct gcaccgcata      6900
gcagatctat tggagaagaa gctttcctca gaaatctcga ggggagccag ggcagaacag      6960
cgggtggcac catcacccgc acctcaagcg aagatgacct cttacaaacc gaaagtcggg      7020
agctcaccta cccgaaaaac tccgctgtcc acttcgccca caaggagtg gacacggatt       7080 actcgaaaga aggaagcgag tgtcccgagt caggggacgg gaacacgcca agccatcttt      7140
ccgacgcctt cgccctcaaa tgaggatgga agaagagcg ccatcgcgct ggctcctttc       7200
taccccgacg tcctcttcat caggggaga ttggagttag cacccgtctt caacgatgag       7260
ccaaccatgc aagggaaga gcctccccag cgtgaggcgc gacgacgag gaatagaagc        7320 cagaacgtgc ggcgacatca cgaggctggg gaacgggatc cggcgcaacc cgtatcccgg      7380
gacgaagctt tagaagtagg aaaaactccc gacgagtggg tacaccgaga aaggcggaac      7440
tctcgccgcc gtgatcgccg acaagcttag gaccgagaac gagagcaagc cgagcaaggt      7500
gcaaggctgc gccgagagaa tgctctcttt gctcggaacc tgtaccccga cttcgctcgt      7560
gcaatgaaca cgccgagtga agtcggaggg gtactggccc agatagctga cggcctcccg      7620
cgaaccctag acacggaagg ctaccggcgg ctgcttactc gagcagttaa tcaccttcta      7680
cccatcacta atcctccaag cgacctacgc catgccatca acagccggcg agacacgcgg      7740
agctccatca acgcttcgcg cgaccgatga cacgaaagtg agatagggaa ccgagaggag      7800
tatgtccgag atcatgccat cctggcatga agtcatgcca cccgagctga gtcggttgcg      7860
gcctcgacca gtgtcccgtt ccagggacga tcaagatgac acacaactgg ctcccctcct      7920
tgggaccgac ctcacgaacg ccgacatgaa gacacgtgcg gagtcttcgc acttactccg      7980
tgtctccggg ccatccagtg gcccctaact tcaaggtctc caacgtcagc aagtatgagc      8040
gcaagcagga cctgggtggc tggttagcca tctacacgat tgtcacatgg gccgccggag      8100
cgacggagga cgtgatgaca gtgtattttc ccattgtcct agggcaagac gcaatgcagt      8160
ggctccgaca tctaccccaa cattgcatag acaattggag cgacttcagt tggtgcttca      8220
tcgccaactt ccagtccctc tttgacaagc cggcgcagcc atgggaccta aaatccattg      8280
ggcatcaggg cgatgaaacg ctccggttgt acctcaagag gttttagacc atgaggaacc      8340
acacccccga agtcgccgag gcgggggtga ttgaagactt ctaccgagga tccaatgact      8400
cggctttcgt ccgagccata ctccagaaaa gcgtcggcca cctccgaaca cttgttccgg      8460
gaggcagacc tctacatcac cacgattaa cgggcccagg acctcatcgg aggcacgaaa       8520
gccgcgccac acgcgccacg gtgtgacacg aaccagc                                8557
```

-continued

<210> SEQ ID NO 2
<211> LENGTH: 23
<212> TYPE: DNA
<213> ORGANISM: Artificial Sequence
<220> FEATURE:
<223> OTHER INFORMATION: forward event primer

<400> SEQUENCE: 2
attctggctt tgctgtaaat cgt                                            23

<210> SEQ ID NO 3
<211> LENGTH: 24
<212> TYPE: DNA
<213> ORGANISM: Artificial Sequence
<220> FEATURE:
<223> OTHER INFORMATION: event reverse primer

<400> SEQUENCE: 3
ttacaatcaa cagcaccgta cctt                                           24

<210> SEQ ID NO 4
<211> LENGTH: 19
<212> TYPE: DNA
<213> ORGANISM: Artificial Sequence
<220> FEATURE:
<223> OTHER INFORMATION: event probe

<400> SEQUENCE: 4
ctaaccttca ttgtattcc                                                 19

<210> SEQ ID NO 5
<211> LENGTH: 18
<212> TYPE: DNA
<213> ORGANISM: Artificial Sequence
<220> FEATURE:
<223> OTHER INFORMATION: reference forward primer

<400> SEQUENCE: 5
tggcggacga cgacttgt                                                  18

<210> SEQ ID NO 6
<211> LENGTH: 19
<212> TYPE: DNA
<213> ORGANISM: Artificial Sequence
<220> FEATURE:
<223> OTHER INFORMATION: reference reverse primer

<400> SEQUENCE: 6
aaagtttgga ggctgccgt                                                 19

<210> SEQ ID NO 7
<211> LENGTH: 26
<212> TYPE: DNA
<213> ORGANISM: Artificial Sequence
<220> FEATURE:
<223> OTHER INFORMATION: reference probe

<400> SEQUENCE: 7
cgagcagacc gccgtgtact tctacc                                         26

<210> SEQ ID NO 8
<211> LENGTH: 73
<212> TYPE: DNA
<213> ORGANISM: Artificial Sequence
<220> FEATURE:

```
<223> OTHER INFORMATION: event amplicon

<400> SEQUENCE: 8
ttacaatcaa cagcaccgta ccttgaagcg gaatacaatg aaggttagct acgatttaca      60
gcaaagccag aat                                                         73

<210> SEQ ID NO 9
<211> LENGTH: 79
<212> TYPE: DNA
<213> ORGANISM: Artificial Sequence
<220> FEATURE:
<223> OTHER INFORMATION: reference amplicon

<400> SEQUENCE: 9
tggcggacga cgacttgtcc gagcagaccg ccgtgtactt ctacctgctc aagggcacgg      60
acggcagcct ccaaactttt                                                  79
```